United States Patent [19]

Wingen et al.

[11] Patent Number: 5,025,097
[45] Date of Patent: Jun. 18, 1991

[54] 4-CHLOROOXAZOLE DERIVATIVES AND PROCESSES FOR THEIR PREPARATION AND USE

[75] Inventors: Rainer Wingen, Hattersheim; Dieter Guenther, Kelkheim; Juergen Lingnau, Mainz-Laubenheim, all of Fed. Rep. of Germany

[73] Assignee: Hoechst Aktiengesellschaft, Frankfurt am Main, Fed. Rep. of Germany

[21] Appl. No.: 424,556

[22] Filed: Oct. 20, 1989

Related U.S. Application Data

[62] Division of Ser. No. 162,596, Mar. 1, 1988, Pat. No. 4,892,799.

[30] Foreign Application Priority Data

Mar. 4, 1987 [DE] Fed. Rep. of Germany ....... 3706880

[51] Int. Cl.$^5$ .......................................... C07D 263/34
[52] U.S. Cl. ..................................... 548/235; 546/94; 546/275
[58] Field of Search .................... 548/235; 546/94, 275

[56] References Cited

U.S. PATENT DOCUMENTS

| | | | |
|---|---|---|---|
| 2,726,246 | 12/1955 | Trosken | 548/235 |
| 2,751,383 | 6/1956 | Trosken | 548/235 |
| 4,371,606 | 2/1983 | Dönges | 548/235 |
| 4,371,607 | 2/1983 | Donaes | 548/235 |

FOREIGN PATENT DOCUMENTS

| | | | |
|---|---|---|---|
| 0041675 | 12/1981 | European Pat. Off. | 548/235 |
| 2844394 | 4/1980 | Fed. Rep. of Germany | 548/235 |
| 0963248 | 5/1985 | U.S.S.R. | 548/235 |

OTHER PUBLICATIONS

Zaugg et al., Jour. Org. Chem., vol. 36, pp. 1937–1941, (1971).
Fowler et al., Jour. Am. Chem. Soc., vol. 90, pp. 2875–2881, (1968).
Chem. Abstr., vol. 110, entry 95213y, (1989), Abstracting Wingen, DE 3706880, (1988).
Chem. Abstr., vol 108, entry 13841y, (1988), (Wiedemann).
CHem. Abstr., vol. 110, entry 125315c, (1989).

*Primary Examiner*—Donald G. Daus
*Attorney, Agent, or Firm*—Foley & Lardner

[57] ABSTRACT

The invention relates to 4-chlorooxazole derivatives of the general formula I

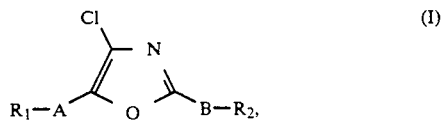

which carry an unsaturated group in the 2- or 5-position, e.g., the —CH=CH— or —CH=CH—CH=CH— group.

In the formula $R_1$ is phenyl, which is optionally substituted in one or more positions by ($C_1$-$C_4$)-alkoxy or di-($C_1$-$C_4$)-alkylamino radicals and $R_2$ is phenyl, phenyloxazolyl, pyridyl, julolidin-9-yl, N-($C_1$-$C_4$-alkyl)-carbazol-3-yl, coumarin-6-yl, or stilben-4-yl, which are optionally substituted in one or more positions by ($C_1$-$C_4$)-alkyl, ($C_1$-$C_4$)-alkoxy, halogen-($C_1$-$C_4$)-alkoxy, hydroxy, halogen, di-($C_1$-$C_4$)-alkylamino, or dibenzylamino radicals.

The compounds are used as photoconductive substances.

4 Claims, No Drawings

4-CHLOROOXAZOLE DERIVATIVES AND PROCESSES FOR THEIR PREPARATION AND USE

This application is a division of application Ser. No. 07/162,596, filed Mar. 1, 1988, now U.S. Pat. No. 4,892,799.

BACKGROUND OF THE INVENTION

The present invention relates to new 4-chlorooxazole derivatives, processes for their preparation and their use.

European Patent No. 0 010 652 discloses 4-chlorooxazole derivatives and the preparation and use thereof in photoconductive layers and as optical brighteners. The compounds are prepared by condensing an acyl cyanide with an aldehyde in the presence of hydrogen chloride. However, 4-chlorooxazole derivatives carrying unsaturated groups in the 2- or 5-position cannot be prepared according to this known method since, in the condensation reaction, there is also an addition of hydrogen chloride at the double bond.

SUMMARY OF THE INVENTION

It is therefore an object of the present invention to provide 4-chlorooxazole derivatives having unsaturated groups at the 2- or 5-position in substantially pure form.

It is a further object of the present invention to provide 4-chlorooxazole derivatives without addition at the unsaturated groups.

It is yet another object of the present invention to provide 4-chlorooxazole derivatives without hydrogen chloride addition at the unsaturated groups.

It is a further object of the present invention to provide processes for obtaining 4-chlorooxazole derivatives having unsaturated groups at the 2- or 5-position in substantially pure form.

In accordance with these and other objects, the present invention provides 4-chlorooxazole derivatives of the general formula I in substantially pure form wherein

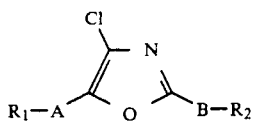

(I)

A is a single bond or the —CH=CH— group,
B is a single bond, the —CH=CH— or —CH=CH—CH=CH— group, and is a single bond in the case of A representing the —CH=CH-group,
$R_1$ phenyl, which is optionally substituted in one or more positions by ($C_1$-$C_4$)-alkoxy or di-($C_1$-$C_4$)-alkylamino radicals, and
$R_2$ phenyl, phenyloxazolyl, pyridyl, julolidin-9-yl, N-($C_1$-$C_4$-alkyl)-carbazol-3-yl, coumarin-6-yl or stilben-4-yl, which are optionally substituted in one or more positions by ($C_1$-$C_4$)-alkyl, ($C_1$-$C_4$)-alkoxy, halogen-($C_1$-$C_4$)-alkoxy, hydroxy, halogen, di-($C_1$-$C_4$)-alkylamino or dibenzylamino radicals.

The preferred compounds of the general formula I are those, in which
A is a single bond,
B is the —CH=CH— group,
$R_1$ is phenyl, which is substituted by ($C_1$-$C_4$)-alkoxy radicals, and
$R_2$ is phenyl or N-($C_1$-$C_4$-alkyl)-carbazol-3-yl, which are substituted by ($C_1$-$C_4$)-alkoxy, halogen, hydroxy and/or di-($C_1$-$C_4$)-alkylamino radicals.

Particularly suitable compounds of the general formula I are those, in which
A is a single bond,
B is the —CH=CH— group,
$R_1$ is methoxyphenyl, and
$R_2$ is p-ethoxyphenyl, p-dimethylaminophenyl, p-diethylaminophenyl, o-chloro-p-dimethylaminophenyl, o-hydroxy-p-diethylaminophenyl or N-ethylcarbazol-3-yl.

The invention also provides processes for the preparation of the 4-chlorooxazole derivatives of the present invention, corresponding to the general formula I. In the processes according to the present invention the unsaturated structural elements A or B, resp., carrying the respective substituents $R_1$ and $R_2$ and a corresponding 4-chlorooxazole compound are condensed in the presence of a base and the 4-chlorooxazole derivative is isolated from the reaction mixture and dried.

The process may comprise the steps of condensing a compound of general formula II

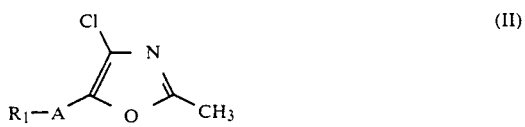

(II)

wherein
A is a single bond, and
$R_1$ is defined as above with a compound of general formula III

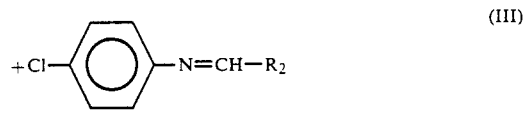

(III)

wherein $R_2$ is defined as above in an inert organic solvent in the presence of a base, at a temperature in the range from about 20° C. to 80° C., to form a compound of general formula I, in which A is a single bond and B is the —CH=CH— group; and separating said compound of formula I from said reactants.

Alternatively the process may comprise the steps of condensing a compound of general formula IV

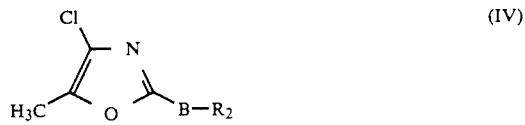

(IV)

wherein
B is a single bond, and
$R_2$ is defined as above with a compound of the general formula V

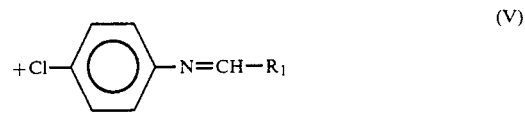

(V)

wherein $R_1$ is defined as above in an inert solvent in the presence of a base, at a temperature in the range from about 0° C. to 40° C., to form a compound, in which A is the —CH=CH— group and B is a single bond; and separating said compound of general formula I from said reactants.

Another process which may be used comprises the steps of condensing a phosphonium salt corresponding to general formula VI

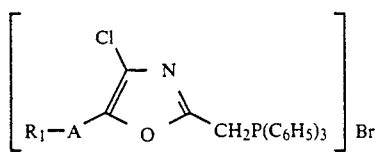
(VI)

wherein
A is a single bond, and
$R_1$ is defined as above with an aldehyde corresponding to the general formula VII $X—R_2$ (VII)

wherein $R_2$ is defined as above, and X stands for —CHO or —CH=CH—CHO, in an inert organic solvent in the presence of a base, at about room temperature, to form a compound, in which A is a single bond and B is the —CH=CH— or the —CH=CH—CH=CH— group; and separating said compound of general formula I from said reactants.

DESCRIPTION OF THE PREFERRED EMBODIMENTS

In one process for the preparation of a compound corresponding to the general formula I, a compound of the formula II

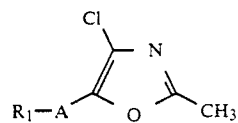
(II)

in which A and $R_1$ have the indicated meanings, is condensed with a compound of the formula III

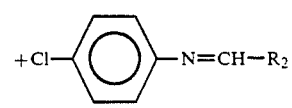
(III)

in which $R_2$ has the indicated meaning, in an inert organic solvent in the presence of a base, at a temperature in the range from about 20° C. to 80° C., to form a compound in which A is a single bond and B is the —CH=CH-group. The compound so produced is separated, dried and optionally purified by reprecipitation (Process A). It is preferred to perform the condensation reaction at a temperature in the range from about 40° C. to 60° C. and to use dimethyl formamide as the solvent and potassium hydroxide as the base.

In another process for the preparation of a compound corresponding to the general formula I, a compound of the formula IV

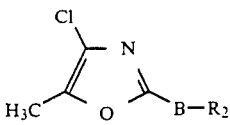
(IV)

in which B and $R_2$ have the indicated meanings, is condensed with a compound of the formula V

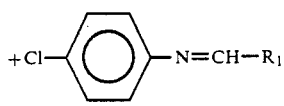
(V)

in which $R_1$ has the indicated meaning, in an inert solvent in the presence of a base, at a temperature in the range from about 0° C. and 40° C., to form a compound, in which A is the —CH=CH— group and B is a single bond. The compound so produced is separated and optionally purified by reprecipitation. It is preferred to perform the condensation reaction at a temperature in the range from about 20° C. to 30° C. (Process B).

A compound corresponding to the general formula I can also successfully be prepared with the aid of a process in which a phosphonium salt corresponding to the formula VI

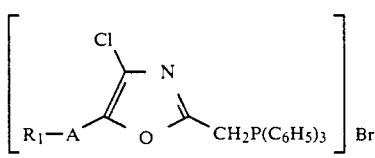
(VI)

in which A and $R_1$ have the indicated meanings, is condensed with an aldehyde corresponding to the formula VII $X—R_2$ (VII)

in which $R_2$ has the indicated meaning and X stands for —CHO or —CH=CH—CHO, in an inert organic solvent in the presence of a base at room temperature to form a compound in which A is a single bond and B is the —CH=CH— group or the —CH=CH—CH=CH— group. The compound so produced is separated from the reaction mixture, dried and optionally purified by reprecipitation (Process C). The preferred solvent used comprises dimethyl sulfoxide and the preferred base comprises dimethylsulfinyl sodium.

The combination is effected by condensing 2-methyl-4-chlorooxazoles of the formula II (Process A) or 5-methyl-4-chlorooxazoles of the formula IV (Process B) with appropriate derivatives of aldehydes (III or V, respectively), according to a method for methyl heterocycles described by I. J. Fletcher, A. E. Sigrist in "Adv. Heterocyclic Chem.", A. R. Katritzky, A. J. Bowlton, eds., Academic Press, New York, 1978, vol. 23, p. 171.

It is also advantageous to condense aldehydes VII with triphenylphosphinium compounds of the 4-chlorooxazole VI, under conditions which are customarily used within the scope of Wittig reactions ("Neuere Methoden der Organischen Chemie" ["Recent Methods of Organic Chemistry"], W. Foerst, ed., Verlag Chemie Winheim, 1967, volume V, p. 1) (Process C).

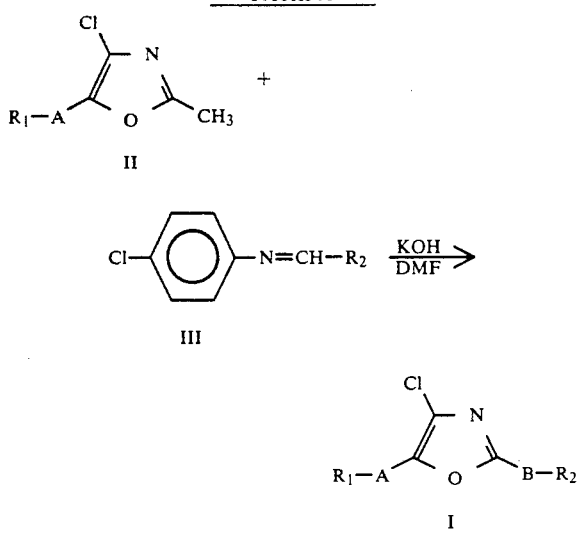

Reaction Scheme 1
Process A

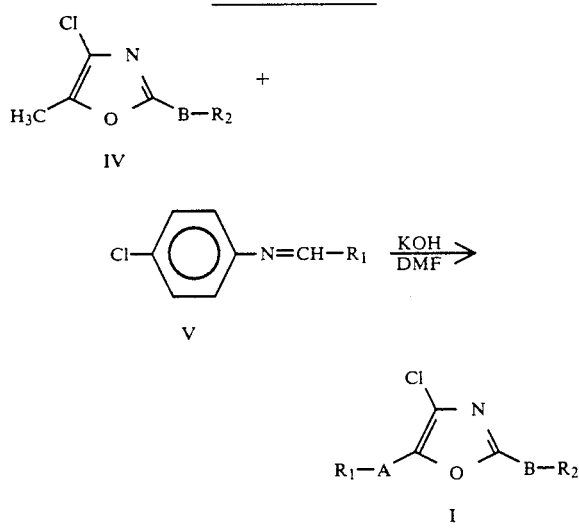

Reaction Scheme 2
Process B

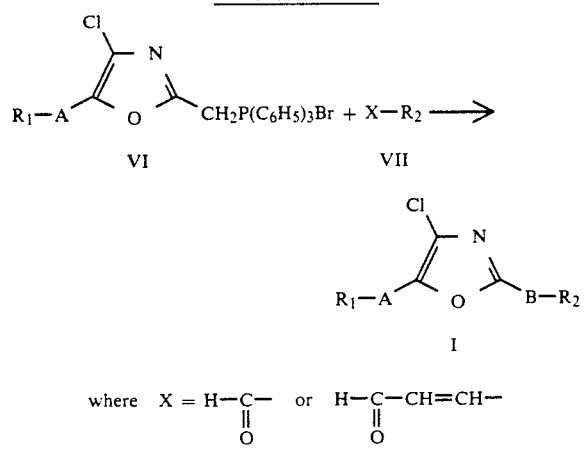

Reaction Scheme 3
Process C

The 4-chlorooxazoles II and IV which are required as the starting materials are readily obtainable according to methods known from the literature, as described in European Patent 0 010 652, for example, by hydrogen chloride-catalyzed condensation of substituted benzoyl cyanides with acetaldehyde (in the case of II) or by an analogous reaction of acetyl cyanide (pyruvonitrile) with aldehydes (in the case of IV).

The compounds VI are obtainable by methods known from the literature (Houben-Weyl, "Methoden der Organischen Chemie" ["Methods of Organic Chemistry"], Vol. V, 1b, page 383, E. Mueller, ed., G. Thieme Verlag, 1972), from the corresponding bromomethyl oxazoles which, in turn, are readily available, for example, by brominating compounds II or IV.

The compounds of the general formula I are particularly advantageously used as photoconductive substances, for example, in electrophotographic recording materials, comprised of a conductive support and a layer arrangement which has an insulating action in the dark, but is rendered conductive under exposure to light. The layer arrangement may comprise one or more layers. In the case of a single layer, at least one photoconductive substance is dispersed or dissolved in at least one binder and, for example, vapor-deposited directly onto a conductive support. A multi-layer arrangement comprises at least one charge-carrier-generating layer and at least one charge-transporting layer.

Charge images on electrophotographic layers are produced in an exposure step following charging. On exposure, electric charge is first generated and then transported through the layer up to the layer surface, where it neutralizes the charge there present. In the process, photoreceptors in which charge generation and charge transport are effected by the same chemical substance are distinguished from others, in which charge generation is achieved by adding a second substance, i.e., the sensitizer. It is thus possible to practice the electrophotographic process even with light of a wavelength which is not absorbed by the photoconductive substance.

To obtain a homogeneous sensitization the organic dyes listed in Schultz: Dye Tables (7th edition, Volume 1, 1931) are used. These include, for example, triarylmethane dyes, such as Brilliant Green (No. 760, page 314), Victoria Blue B (No. 822, page 347), Methyl Violet (No. 783, page 327), Crystal Violet (No. 785, page 329), Acid Violet 6B (No. 381, page 351); xanthene dyes, i.e., rhodamines, such as Rhodamine B (No. 864, page 365), Rhodamine 6G (No. 866, page 366), Rhodamine G Extra (No. 865, page 366), Sulforhodamine B (No. 863, page 364) and Fast Acid Eosin G (No. 870, page 368), and phthaleins, such as, Eosin S (No. 883, page 375), Eosin A (No. 881, page 374), Erythrosin (No. 866, page 376), Phloxin (No. 890, page 378), Bengal Rose (No. 889, page 378), and Fluorescein (No. 880, page 373); thiazine dyes, such as Methylene Blue (No. 1038, page 449); acridine dyes, such as Acridine Yellow (No. 901, page 383), Acridine Orange (No. 908, page 387), and Trypaflavin (No. 906, page 386); quinoline dyes, such as Pinacyanol (No. 924, page 396) and Cryptocyanine (No. 927, page 397); quinone dyes and ketone dyes, such as Alizarin (No. 1141, page 449), Alizarin Red S (No. 1145, page 502) and Quinalizarin (No. 1148, page 504). Suitable dyes are also cyanine dyes (polymethine dyes), such as Astrazone Yellow 3 G (Color Index [C.I.] No. 48 055) and 5 G (C.I. 48 065), Basic Yellow 52 115 (C.I. 48 060), Astrazone Yellow GRL, Astrazone Orange G (C.I. 48 040) and R (C.I. 48 035) and Astrazone Orange 3R (not yet classified). Pyrylium salts, thiapyrylium salts and benzopyrylium salts can also be used. It is also possible to use mixtures of sensitizing dyes.

Dispersed dyes or pigments can also be used comprising metal-containing or metal-free phthalocyanine pigments, e.g., copper phthalocyanine, perinone, thioindigo, polycyclic quinone, quinacridone, perylene, anthraquinone, dioxazine, azo, bisazo, trisazo and cyanine pigments or benzo(thio)-xanthene derivatives and mixtures thereof.

Particularly preferred are phthalocyanine pigments, such as the various copper phthalocyanine modifications ($\alpha$, $\beta$, $\epsilon$), bis- and trisazo pigments, perylene-3,4,9,10-tetracarboxylic acid anhydride and its imide derivatives or (iso)violanthrones. They can be present in an amount of up to 30%, based on the total weight of the photoconductive layer. The preferred quantities of pigment used are in the range from 0.1% to 10%.

The highly insulating binders used in the charge carrier-generating layer and in the charge transport layer may be identical or different. Binders which are suitable from the point of view of flexibility, film-forming properties and adhesion, comprise natural and synthetic resins which, in the preparation of the layers, incipiently dissolve or swell in customary solvents or solvent mixtures. Resins of this kind include polyester resins, which comprise copolyesters of isophthalic acid and terephthalic acid with glycols. Silicone resins have also proved suitable. Polycarbonate resins can advantageously be used. In the production of printing plates and printed circuits preference is given to binders which are soluble in aqueous or alcoholic solvent systems with an addition of acid or alkali, if appropriate. Aromatic or aliphatic, easily flammable solvents are excluded for physiological and safety reasons. Suitable resin binders therefore comprise high-molecular weight substances carrying groups which render them alkali-soluble. These groups include, for example, acid anhydride, carboxyl, carboxylic acid amide, phenol, sulfonic acid, sulfonamide, or sulfonimide groups. Resin binders with high acid numbers are preferably used. Copolymers containing anhydride groups can successfully be employed since, due to the absence of free acid groups, they have a low dark conductivity and are, nevertheless, readily soluble in alkali. Copolymers of styrene and maleic anhydride, sulfonyl urethanes according to German Offenlegungsschrift 32 10 577 and copolymers of acrylic and methacrylic acid have proved particularly suitable.

The layers contain customary additives comprising substances which are added to the coating solutions and thus improve the surface texture and flexibility of the layers. The additives may include, for example, plasticizers, such as triphenyl phosphate, and levelling agents, such as silicone oils.

Suitable electrically conductive layer supports are comprised of materials having adequate electrically conducting properties, such as those conventionally used for this purpose. The layer support may be in the form of a flexible web or a plate. In a preferred embodiment the layer support is suited for the production of printing plates and printed circuits and comprises, for example, an aluminum, zinc, magnesium, copper, iron, nickel or multi-metal plate. It is also possible to use metallized supports, for example, vacuum-metallized plastic films, such as polyester films vacuum-metallized with aluminum or copper-clad polyimide films and plates.

Surface-finished layer supports of aluminum have proved particularly suitable. Surface finishing comprises a mechanical or electrochemical graining treatment, optionally followed by anodization and treatment with polyvinyl phosphonic acid, according to German Offenlegungsschrift No. 16 21 478, corresponding to U.S. Pat. No. 4,153,461.

In general, an insulating intermediate layer can be present on the layer support, for example, a thermally, anodically or chemically produced metal oxide layer, such as an aluminum oxide layer. This barrier layer serves to reduce or prevent charge-carrier injection in the dark, from the electrically conductive layer support into the charge carrier-generating layer. The barrier layer also favorably influences adhesion of the following layers to the layer support. Organic barrier layers can comprise various natural or synthetic resin binders which adhere well to a metal or aluminum surface and are not incipiently dissolved or even detached in the subsequent application of the further layers. The organic barrier layer has a thickness of about 1 $\mu$m, and a metal oxide layer has a thickness in the range from 10 to $10^4$ nm.

For example, in the production of printed circuits, as conventionally used in electronics, the photoconductive layer may initially be applied to an intermediate support, from which it is subsequently transferred to the layer support, in the form of a so-called dry resist. The dry resist may, e.g., be transferred by lamination. Plastic films, such as polyester films, especially polyethylene terephthalate films, have proved particularly suitable for use as intermediate supports.

The coatings are applied in the customary manner, for example, by doctor knife or spray coating. Preference is given to flow-coater application. The layers are, for example, dried in drying channels, the different drying stages being determined by the temperatures in the individual zones, by the travelling speed of the material and by the prevailing rate of air flow.

Below, the syntheses of the compounds corresponding to the general formula I, in accordance with the respective processes A, B or C are explained in detail by means of general working instructions; the compounds I prepared are compiled in Table 1.

TABLE 1
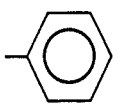
I
| No. | A | R₁ | B | R₂ | M.P. [°C.] | Process |
|---|---|---|---|---|---|---|
| Ia | Single Bond | 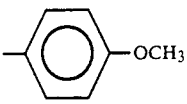 | —CH=CH— | 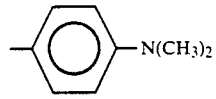 | 128–129 | A |
| b | " | " | " | 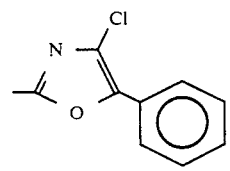 | 124–125 | A |
| c | " | " | " | 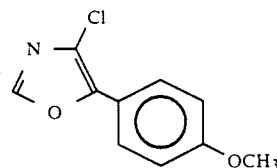 | 188–189 | C |
| d | " | " | " | 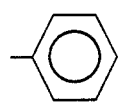 | 175–176 | C |
| e | " | " | —CH=CH—CH=CH— | 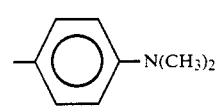 | 99–100 | C |
| f | " | " | " | 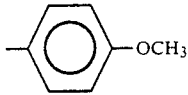 | 142–143 | C |
| g | " | 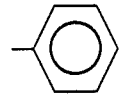 | —CH=CH— | 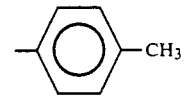 | 106–107 | C |
| h | " | " | " | 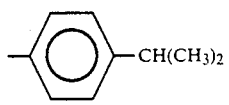 | 124–125 | C |
| i | " | " | " | 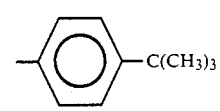 | 76–77 | C |
| j | " | " | " | 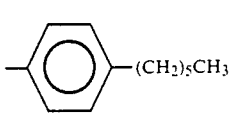 | 91–92 | C |
| k | " | " | " |  | 67–68 | C |

TABLE 1-continued $$R_1-A\overset{Cl}{\underset{O}{=}}\overset{N}{\underset{}{=}}B-R_2 \qquad I$$

| No. | A | R₁ | B | R₂ | M.P. [°C.] | Process |
|-----|---|-----|---|-----|------------|---------|
| l | " | " | " | —C₆H₄—OCH₃ (4-) | 159–160 | A |
| m | " | " | " | —C₆H₄—OC₂H₅ (4-) | 130–131 | C |
| n | " | " | " | —C₆H₄—OCF₂CF₂H (4-) | 104–105 | C |
| o | " | " | " | —C₆H₄—N(CH₃)₂ (4-) | 171–172 | A |
| p | " | " | " | —C₆H₄—N(C₂H₅)₂ (4-) | 107–108 | C |
| q | " | " | " | 2-Cl, 4-N(CH₂C₆H₅)₂—C₆H₃— | 143–144 | C |
| r | " | " | " | 2-Cl, 4-N(CH₃)₂—C₆H₃— | 166–169 | C |
| s | " | " | " | 2-OH, 4-N(C₂H₅)₂—C₆H₃— | 210–211 | C |
| t | " | " | " | 2-OC₂H₅, 4-N(C₂H₅)₂—C₆H₃— | 92–95 | C |
| u | " | " | " | 4-pyridyl | 134–135 | C |

TABLE 1-continued
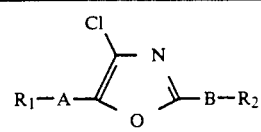
| No. | A | R₁ | B | R₂ | M.P. [°C.] | Process |
|-----|---|----|----|----|------------|---------|
| v | " | " | " | 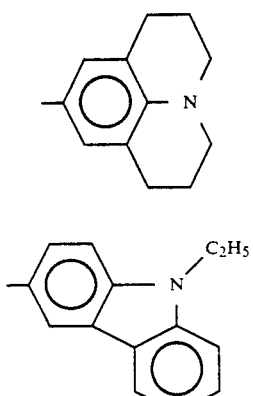 | 137–139 | C |
| w | " | " | " | 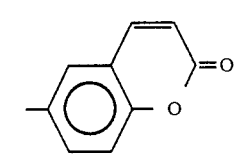 | 175–176 | C |
| x | " | " | " | 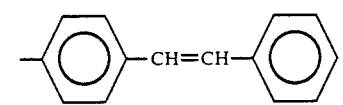 | 211–212 | C |
| y | " | " | " | 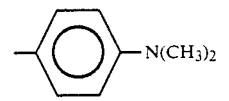 | 193–194 | C |
| z | " | " | —CH=CH—CH=CH— | 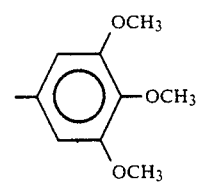 | 158–160 | C |
| aa | " | 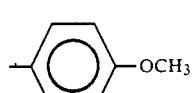 | —CH=CH— | 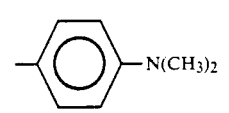 | 138–139 | C |
| ab | " | " | " | 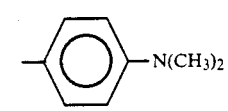 | 205–207 | C |
| ac | " | 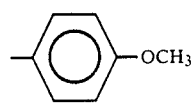 | " | 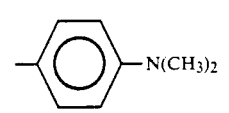 | 138–139 | A |
| ad | " | " | " | 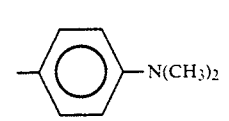 | 154–155 | A |

TABLE 1-continued $$R_1-A-\underset{O}{\underset{\|}{C(Cl)=C}}-B-R_2 \quad \text{I}$$

| No. | A | $R_1$ | B | $R_2$ | M.P. [°C.] | Process |
|---|---|---|---|---|---|---|
| ae | " | " | " | phenyl-(N-ethyl)-carbazolyl group | 178–180 | B |
| af | —CH=CH— | 4-N(CH$_3$)$_2$-phenyl | Single Bond | 4-OCH$_3$-phenyl | 164–165 | B |
| ag | " | " | " | 4-N(CH$_3$)$_2$-phenyl | 195–196 | B |

Process A—General Instruction 160 mmols of potassium hydroxide powder are added to a solution of 40 mmols of 2-methyl-4-chlorooxazole II and 50 mmols of N-(4-chlorophenyl)-R$_2$-azomethine III in 100 ml of dimethyl formamide. Within 30 minutes the reaction mixture is heated to 60° C. and is kept at this temperature for 2 hours. After cooling to 20° C., 400 ml of methanol are added, followed by cooling to −10° C. The solid substance is then separated and recrystallized from methylglycol.

Elementary Analysis for 1-[4-chloro-5-(4-methoxy)-phenyl-oxazol-2-yl]-2-(4-dimethylamino)-phenylethene, i.e., general formula I, wherein:
$R_1$ = 4-methoxyphenyl
A = single bond
B = —CH=CHC—
$R_2$ = 4-dimethylaminophenyl:
$C_{20}H_{19}ClN_2O_2$ calculated: C 67.7, H 5.4 Cl 10.0 N 7.9. found: C 67.8, H 5.3, Cl 10.3, N 7.9.

Process B—General Instruction

A solution of 17 mmols of 5-methyl-4-chlorooxazole IV, 21 mmols of N-(4-chlorophenyl)-R$_1$-azomethine V and 68 mmols of potassium hydroxide powder in 40 ml of dimethyl formamide is stirred for 2 hours at 20° C. After adding 160 ml of methanol, the reaction mixture is cooled to −10° C. and the solid substance is separated and recrystallized from methylglycol.

Elementary Analysis for 1-[4-chloro-2-(4-dimethylamino)phenyl-oxazol-5-yl]-2,4-dimethylamino)-phenyl-ethene, i.e., general formula, I wherein:
$R_1$ = 4-dimethylaminophenyl
A = —CH=CH—
B = single bond
$R_2$ = 4-dimethylaminophenyl:
$C_{21}H_{22}ClN_3O$ calculated: C 68.6, H 6.0, Cl 9.6, N 11.4. found: C 68.4, H 6.1, Cl 9.7, N 11.4.

Process C—General Instruction 60 mmols of sodium hydride (80% suspension) and 100 ml of dimethyl sulfoxide are reacted, finally by heating to 75° C. 60 mmols of finely powdered triphenyl phosphonium salt VI are added to the cooled solution, and after the salt has dissolved, stirring is continued for 50 minutes at 25° C. 60 mmols of aldehyde VII are then added dropwise, and the mixture is stirred for 2 hours at 25° C. and for 3 hours at 75° C. The solid substance obtained after hydrolysis with 500 ml of ice water is recrystallized from methylglycol.

Elementary Analysis for 1-[4-chloro-5-phenyl-oxazol-2-yl]-2-[4-chloro-5-(4-methoxy)-phenyl-oxazol-2-yl]-ethene, i.e., general formula I, wherein:
$R_1$ = phenyl
A = single bond
B = —CH=CH—
$R_2$ = 4-chloro-5-(4-methoxy)-phenyl-oxazol-2-yl:
$C_{21}H_{14}Cl_2N_2O_3$ calculated: C 61.0, H 3.4, Cl 17.2, N 6.8. found: C 60.8, H 3.5, Cl 17.6, N 6.6.

COMPARISON EXAMPLE 1

According to the instruction given in European Patent 0 010 652, a solution of 100 mmols of 4-methoxybenzoyl cyanide and 100 mmols of cinnamaldehyde in 50 ml of tetrahydrofuran is saturated with hydrogen chloride at 0° C. After the mixture has been allowed to stand for 10 hours at 0° C. it is poured onto 200 g of ice, extracted with dichloromethane and the extract obtained is washed and dried. By means of column chromatography on silica gel with elution by dichloromethane, a chlorooxazole-containing fraction can be separated as the main constituent.

According to analysis by gas chromatography, the unsaturated condensation product, corresponding to compound Ig in Table 2 prepared by another route, is only present in an amount of 19.4%.

The main constituent comprises compounds containing a 1,2-substituted chlorethyl unit, which together amount to 68.1%, as determined by $^1$H-NMR analysis.

Separation of this mixture by means of chromatography, distillation or crystallization proves impractical.

Examples of Application:

Different coating formulations were used to test the electrophotographic properties of the compounds of this invention, corresponding to the general formula I.

Coating Formulation 1

15.0 g of Hostaperm Orange GR (Pigment Orange 43, C.I. 71.105) were added to a solution of 10 g of polybutylmethacrylate (®Plexigum P 676, manufacturers Roehm GmbH) in 200 g of tetrahydrofuran and dispersed by milling in a ball mill for 2 hours. After adding 32 g of polymethylmethacrylate (®Plexigum M 345) in 340 g of tetrahydrofuran, the layer was applied to a polyethylene terephthalate film vacuum-metallized with aluminum at a layer weight of 6 g/m$^2$ and was dried. The dried layer was then treated with a 5% solution of the compounds of the invention in tetrahydrofuran and again dried.

Coating Formulation 2

5 g of the compounds according to the invention, 5 g of a copolymer of a maleic acid half-ester and styrene, decomposition point 200° C. to 240° C., and 0.05 g of Rhodamine B were dissolved in 90 g of tetrahydrofuran and applied to a grained and anodized aluminum support for offset printing plates in such a way that a dry layer weight of 6 g/m$^2$ resulted.

Coating Formulation 3

A polyethylene terephthalate film vacuum-metallized with aluminum was first coated by sublimation with a charge-carrier-generating layer of N,N'-dimethylperylene-3,4,9,10-tetracarboxylic acid diimide to give a layer weight of 200 mg/m$^2$. This layer was coated with a solution comprising 50 parts by weight of the substances according to the invention and 50 parts by weight of a polyester (®Dynapol L 206, manufacturers Dynamit Nobel), such that this charge transport layer had a layer weight of 10.5 g/m$^2$.

The results of electrophotographic investigations carried out on the layers prepared according to the examples are compiled in the following Table 2. In the table $E_{\frac{1}{2}}$, $E_{\frac{1}{4}}$ and $E_{\frac{1}{8}}$ refer to the exposure energies in $\mu J/cm^2$, which must be applied at a light intensity of 3 $\mu W/cm^2$ to produce a discharge from the original charge $U_o$ to 0.5 $U_o$, 0.25 $U_o$ and 0.125 $U_o$, respectively. The samples according to coating formulation 1 were measured at 485 nm and the samples according to coating formulations 2 and 3 were measured in white light (halogen-tungsten lamp, heat-absorption glass filter at 650 nm). $U_e$ denotes the residual charge which remains on the layer after exposure for 10 seconds.

COMPARISON EXAMPLE

For comparison, investigations were also carried out on the coating formulations using compounds IX (German Patent 10 58 836) and VIII (European Patent 0 010 652). Coating formulation 1 was, for comparison, also used without post-treatment with a photoconductor-containing solution.

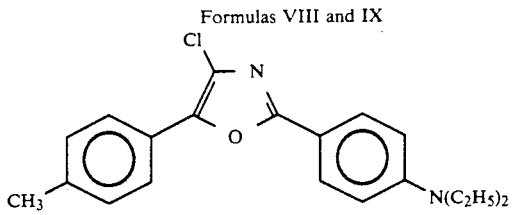

Formulas VIII and IX

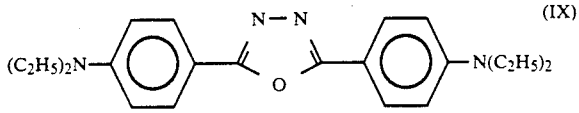

TABLE 2

| Compound | Formul. | $U_o$ | $U_e$ | $E_{\frac{1}{2}}$ | $E_{\frac{1}{4}}$ | $E_{\frac{1}{8}}$ |
| --- | --- | --- | --- | --- | --- | --- |
| Iac | 1 | −406 | −63 | 16.4 | 25 | |
| Iad | 1 | −462 | −47 | 11 | 14 | 32 |
| Ie | 1 | −430 | −67 | 21.6 | 70 | |
| If | 1 | −39 | −15 | 70.6 | | |
| Ih | 1 | −770 | −39 | 6.1 | 8 | 13 |
| Ii | 1 | −857 | −47 | 5.7 | 7 | 10 |
| In | 1 | −734 | −31 | 5.9 | 8 | 11 |
| Ir | 1 | −857 | −23 | 3.7 | 4.7 | 6.1 |
| Is | 1 | −647 | −23 | 3.6 | 5.2 | 8.2 |
| Iw | 1 | −632 | −47 | 9 | 23 | 67 |
| Iy | 1 | −193 | −51 | 59.5 | | |
| Iz | 1 | −308 | −59 | 27.5 | 96 | |
| without | 1 | −746 | −319 | 75 | | |
| VIII | 1 | −525 | −75 | 20.4 | 62 | |
| IX | 1 | −620 | −7 | 5.7 | 7 | 10 |
| Iac | 2 | −268 | −31 | 20.7 | 51 | |
| Iad | 2 | −165 | −15 | 19.7 | 50 | 99 |
| Iaf | 2 | −529 | −177 | 70.4 | | |
| Ie | 2 | −481 | −240 | 146 | | |
| If | 2 | −493 | −51 | 16.9 | 47 | 126 |
| Ig | 2 | −623 | −470 | | | |
| In | 2 | −596 | −55 | 12 | 25 | 47 |
| Ij | 2 | −722 | −481 | | | |
| Il | 2 | −169 | −3 | 19.1 | 41 | 65 |
| Io | 2 | −292 | −3 | 10.7 | 27 | 49 |
| Ip | 2 | −730 | −94 | 11.7 | 28 | |
| Iw | 2 | −647 | −7 | 7.9 | 18 | 36 |
| Iz | 2 | −406 | −165 | 101 | | |
| VIII | 2 | −398 | −11 | 10.6 | 30 | 62 |
| IX | 2 | −426 | −7 | 8 | 20 | 39 |
| Ik | 3 | −647 | −181 | 4.7 | | |
| Im | 3 | −556 | 0 | 1.7 | 3.2 | 5 |
| It | 3 | −339 | 0 | 2.3 | 4.8 | 7.5 |
| IX | 3 | −205 | −7 | 4.9 | 10.1 | 18.4 |

What is claimed is:

1. A 4-Chlorooxazole represented by formula I

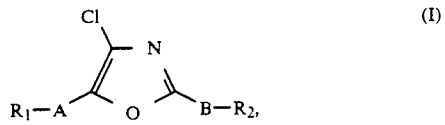

wherein

A is a single bond or a —CH=CH— group,

B is a single bond when A is the —CH=CH— group, and a —CH=CH— or —CH=CH—CH=CH— group when A is a single bond, $R_1$ is phenyl, which is unsubstituted or substituted in one or more positions by ($C_1$-$C_4$)-alkoxy or di-($C_1$-$C_4$)-alkylamino radicals, and $R_2$ is N-($C_1$-$C_4$-alkyl)-carbazol-3-yl, which is unsubstituted or substituted in one or more positions by ($C_1$-$C_4$)-alkyl, ($C_1$-$C_4$)-alkoxy, halogen-($C_1$-$C_4$)- alkoxy, hydroxy, halogen, di-$(C_1-C_4)$-alkylamino or dibenzylamino radicals.

2. A compound as claimed in claim 1, wherein
A is a single bond,
B is the —CH=CH— group,
$R_1$ is phenyl, which is substituted by $(C_1-C_4)$-alkoxy radicals, and
$R_2$ is N-$(C_1-C_4$-alkyl)-carbazol-3-yl, which are substituted by $(C_1-C_4)$-alkoxy, halogen, hydroxy or di-$(C_1-C_4)$-alkylamino radicals.

3. A compound as claimed in claim 1 wherein
A is a single bond,
B is the —CH=CH— group,
$R_1$ is methoxyphenyl, and
$R_2$ is N-ethylcarbazol-3-yl.

4. A compound as claimed in claim 2 wherein
A is a single bond,
B is the —CH=CH— group,
$R_1$ is methoxyphenyl, and
$R_2$ is N-ethylcarbazol-3-yl.

* * * * *